(12) United States Patent
Pratt et al.

(10) Patent No.: US 9,377,435 B2
(45) Date of Patent: Jun. 28, 2016

(54) AUXILIARY GAS DIFFUSION ELECTRODES FOR DIAGNOSTICS OF ELECTROCHEMICAL GAS SENSORS

(71) Applicant: LIFE SAFETY DISTRIBUTION AG, Uster (CH)

(72) Inventors: Keith Francis Edwin Pratt, Portsmouth (GB); Martin G. Jones, Havant (GB); John Chapples, Portsmouth (GB)

(73) Assignee: Honeywell International Inc., Morris Plains, NJ (US)

( * ) Notice: Subject to any disclaimer, the term of this patent is extended or adjusted under 35 U.S.C. 154(b) by 120 days.

(21) Appl. No.: 13/644,671

(22) Filed: Oct. 4, 2012

(65) Prior Publication Data

US 2013/0087457 A1    Apr. 11, 2013

Related U.S. Application Data

(60) Provisional application No. 61/545,669, filed on Oct. 11, 2011.

(51) Int. Cl.
*G01N 27/404* (2006.01)
*G01N 27/416* (2006.01)

(52) U.S. Cl.
CPC ........ *G01N 27/4045* (2013.01); *G01N 27/4163* (2013.01)

(58) Field of Classification Search
CPC ......... G01N 27/404–27/4045; G01N 27/4062; G01N 27/4065; G01N 27/41; G01N 1/2252; B01D 53/32–53/326; G01M 15/10; G01M 15/102; G01M 15/104; F01N 2560/00–2560/20; F01N 2250/00–2550/24; F01N 3/10; F01N 11/00

USPC .............. 204/421–429; 73/23.31, 23.32
See application file for complete search history.

(56) References Cited

U.S. PATENT DOCUMENTS

| | | | |
|---|---|---|---|
| 5,298,146 A * | 3/1994 | Braden et al. ........... | 204/406 |
| 5,558,752 A | 9/1996 | Wang et al. | |
| 5,668,302 A | 9/1997 | Finbow et al. | |
| 5,720,863 A * | 2/1998 | Kim et al. .............. | 204/406 |
| 5,723,036 A | 3/1998 | Chrzan et al. | |
| 5,932,079 A * | 8/1999 | Haupt et al. ............ | 204/415 |
| 6,096,186 A | 8/2000 | Warburton | |
| 6,251,243 B1 | 6/2001 | Lindsay | |

(Continued)

FOREIGN PATENT DOCUMENTS

DE    41 36 779 A1    5/1993
DE    195 33 911 C1    5/1996

(Continued)

OTHER PUBLICATIONS

European Search Report, mailed Feb. 1, 2013, corresponding to European Application No. EP 12 18 7546.

*Primary Examiner* — Jennifer Dieterle
(74) *Attorney, Agent, or Firm* — Conley Rose, P.C.; Kristin Jordan Harkins

(57) ABSTRACT

An electrochemical gas sensor includes additional gas diffusion electrodes incorporated to carry out one or more diagnostic functions while the sensor is responding to a target gas. Members of a plurality of sensing and diagnostic electrodes can be switched by associated control circuits to intermittently sense a target gas while others intermittently sense a different gas. The diagnostic electrodes are in direct communication with the target gas that is entering the cell.

18 Claims, 6 Drawing Sheets

(56) References Cited

U.S. PATENT DOCUMENTS

| | | | |
|---|---|---|---|
| 6,454,923 B1 * | 9/2002 | Dodgson et al. | 204/415 |
| 6,562,208 B2 | 5/2003 | Slater et al. | |
| 7,828,956 B2 * | 11/2010 | Ding et al. | 205/781 |
| 2002/0036137 A1 | 3/2002 | Slater et al. | |
| 2003/0183520 A1 * | 10/2003 | Mabuchi et al. | 204/424 |
| 2005/0145493 A1 * | 7/2005 | Saffell et al. | 204/431 |
| 2006/0096871 A1 * | 5/2006 | Manoukian et al. | 205/782 |
| 2008/0202929 A1 | 8/2008 | Chapples et al. | |
| 2009/0127134 A1 | 5/2009 | Pratt et al. | |
| 2010/0252455 A1 | 10/2010 | Pratt et al. | |
| 2011/0100813 A1 * | 5/2011 | Davis et al. | 204/415 |
| 2012/0193229 A1 | 8/2012 | Tillotson et al. | |

FOREIGN PATENT DOCUMENTS

| | | |
|---|---|---|
| EP | 2 327 981 A3 | 7/2011 |
| WO | WO 01/31326 A1 | 5/2001 |
| WO | WO2010/051345 * | 5/2010 |

* cited by examiner

AUXILIARY GAS DIFFUSION ELECTRODES FOR DIAGNOSTICS OF ELECTROCHEMICAL GAS SENSORS

CROSS-REFERENCE TO RELATED APPLICATION

This application claims the benefit of the filing date of U.S. Provisional Application Ser. No. 61/545,669 filed Oct. 11, 2011, entitled "Auxiliary Electrodes for Diagnostics of Electrochemical Gas Sensors". The '669 application is hereby incorporated herein by reference.

FIELD

The application pertains to gas sensors which include extra electrodes to carry out diagnostics of the respective sensor. More particularly, the application pertains to additional gas diffusion electrodes incorporated in electrochemical gas sensors to carry out diagnostic activities while the respective sensor is in operation.

BACKGROUND

Electrochemical sensors are known and can be used to detect various types of gases including oxygen as well as toxic gases such as carbon monoxide, sulphur dioxide and hydrogen sulfide. Representative sensors have been disclosed in U.S. Pat. No. 5,668,302 to Finbow et al. entitled "Electrochemical Gas Sensor Assembly", issued Sep. 16, 1997, and U.S. Patent Application No. 2010/0252455 published Oct. 7, 2010 and entitled "Methods of Operation of Electrochemical Gas Sensors". Both the '302 patent and the '455 application are commonly owned with the present application and are incorporated herein by reference.

To improve their usefulness, it is desirable that they function as expected. To monitor sensor operation, diagnostic tests and/or remediation processes can be performed on the sensing electrodes of electrochemical gas sensors. Often such processes require the sensor to be out of operation for a length of time due to the time taken to perform the actual process and a subsequent recovery time for the sensing electrode to return to its normal operating state. Such processes include, but are not restricted to, scanning voltammetry to obtain information about sensing electrode activity, or remediation processes such as that described in US201028852A1. It is undesirable for the sensor to be out of operation during such tests.

It is also advantageous to provide means of performing diagnostic tests of various types on electrochemical gas sensors to detect whether the primary gas diffusion access path is operating in the intended mode, or other incorrect/faulty operation modes.

Existing sensor diagnostic tests are often performed by modulating the sensing electrode and monitoring the resulting signal. For example, U.S. Pat. No. 6,251,243 describes a method by which the transient signal resulting from a perturbation to the sensing electrode is used to determine if the sensor is operating correctly. EP 2327981 describes a technique whereby the sensing electrode signal is interrupted to generate a diagnostic. U.S. Pat. No. 5,558,752 and U.S. Pat. No. 6,096,186 describes a means whereby the sensing electrode potential is scanned to measure electrode activity.

Methods such as those described above all potentially suffer from the disadvantage that by perturbing the sensing electrode the sensor may be out of operation for the duration of the test and also may require considerable time (in some cases many hours) to recover back to normal operation following the test. Furthermore, due to the high surface area of typical gas diffusion electrodes any such tests (e.g. scanning voltammetry) need to be performed relatively slowly. This again may result in the sensor being out of use for several hours. As a result such tests can only be performed infrequently, or when the sensor is not in use. For many applications, however, it is desirable to be able to carry out diagnostics more frequently.

Electrochemical gas sensors typically rely on a diffusion limiter such as a membrane or capillary to control access of the target gas to the sensor. There are often also other external restrictions such as protective membranes in the instrument housing. A number of techniques can be used to check the correct internal functioning of such sensors. However they do not test whether the target gas can actually reach the respective sensing electrode and so cannot detect a primary and critical failure mode of electrochemical gas sensors which occurs when such access becomes blocked or restricted. It is therefore desirable to be able to perform a test on an electrochemical gas sensor to ensure that this gas access path is not compromised or blocked, and that the sensing electrode is actually in communication with the ambient air that it is meant to be sampling.

This occurrence may be detected by applying test gas to the sensor, but this is a relatively labour intensive and hence expensive process, particularly for sensors which are located in remote or inaccessible locations. By definition it also requires that the sensor is removed from normal operation, at least for the duration of the test and often for much longer periods to allow for transportation to a test facility.

Many of the existing diagnostic methods such as those described above cannot check the correct operation of the gas access and so offer only partial capture of possible failure modes. There is thus a clear need for improved methods to test whether gas access (capillary, etc.) to toxic sensors (for example) is still functioning, without needing to expose to the target gas.

One solution to this problem uses the fact that, in a CO sensor for example, the platinum sensing electrode can also be used to detect oxygen by running at the appropriate bias potential. This is equivalent to operating the cell as an oxygen pump. Thus, an approach could be to occasionally drive the sensing electrode of a CO sensor to the oxygen reduction potential. The signal generated by oxygen entering through the capillary can be used to check that it is not blocked or restricted, (since oxygen is normally present in the environment). However this is not ideal as the sensor would be out of operation while this was being done and for a significant time afterwards while the electrode recovers back to the operating conditions for CO detection.

Elsewhere in a U.S. Patent Application filed concurrently herewith, and entitled "Auxiliary Micro-electrodes for Diagnostics of Electrochemical Gas Sensors" and assigned U.S. patent application Ser. No. 13/644,485, assigned to the assignee hereof and incorporated herein by reference, we have described methods using a separate, small electrode (microelectrode) or electrodes to perform diagnostics so as to avoid disturbing the operation of the sensing electrode(s) or other electrodes within the sensor. The use of a separate diagnostic electrode avoids interrupting the gas measurement, and the sensor can still operate normally during the diagnostic process.

The above described diagnostic process can be performed quickly and/or continuously by virtue of the fact that the diagnostic electrodes are of a form that allows them to operate without interfering with the other electrodes. However, such approaches cannot meet all the requirements for electrochemical gas sensor diagnostics. For example, there are some measurements of interest in cell diagnostics which cannot adequately be undertaken using a small electrode (microelectrode) due to the low current handling capabilities and consequently low ability to consume target gas.

DETAILED DESCRIPTION

Figure 1:
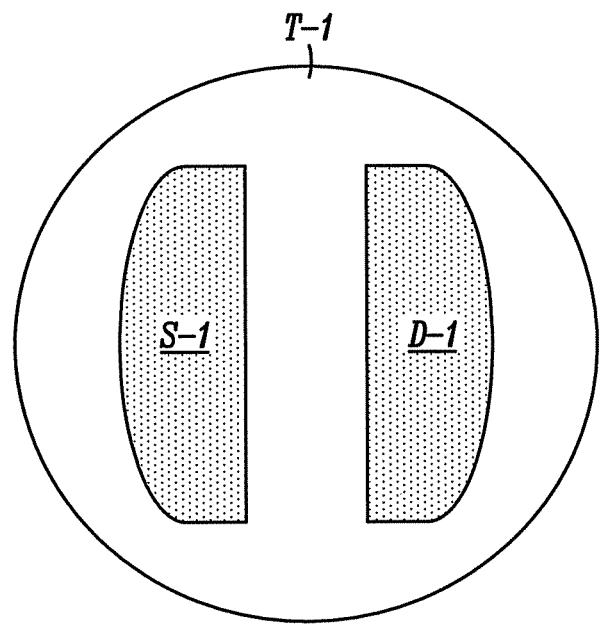
FIG. 1 illustrates a top planar view of sensing and diagnostic electrodes in accordance herewith.
Figure 2:
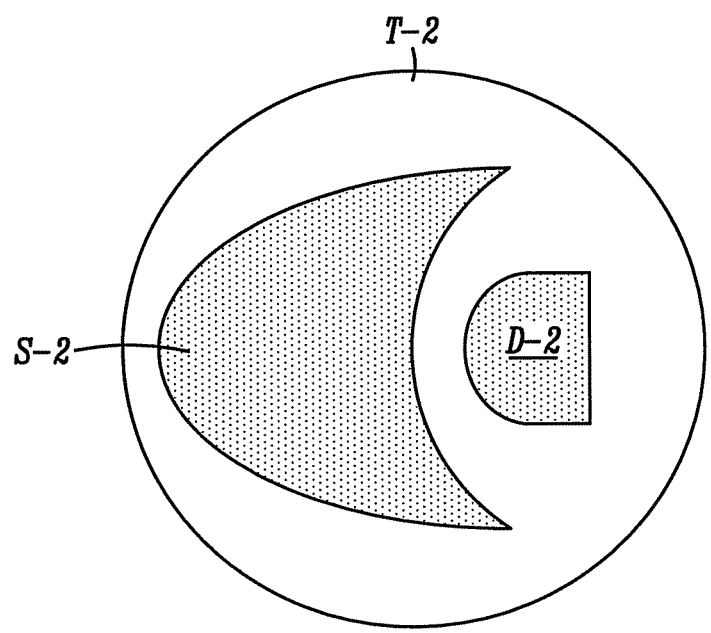
FIG. 2 illustrates a top planar view of another embodiment of sensing and diagnostic electrodes in accordance herewith.

While disclosed embodiments can take many different forms, specific embodiments thereof are shown in the drawings and will be described herein in detail with the understanding that the present disclosure is to be considered as an exemplification of the principles thereof as well as the best mode of practicing same, and is not intended to limit the application or claims to the specific embodiment illustrated.

In summary, embodiments hereof incorporate one or more additional electrodes into an electrochemical gas sensing cell for the purposes of cell diagnostics. The sensor may be a conventional 2, 3 or more electrode (or other) amperometric design. The diagnostic electrode is in direct communication with the incoming target gas passing through the diffusion barrier controlling access to the cell.

In one aspect hereof, the diagnostic electrode(s) is/are preferably gas diffusion electrodes having areas on same scale as the known electrodes used in electrochemical gas sensors. They are preferentially coplanar with the sensing electrode (although other geometries come within the spirit and scope hereof). They can be fabricated, without limitation, using a similar process. In sensors in accordance herewith, the diagnostic electrode(s) is directly exposed to the target gas in the gas phase in parallel with the sensing electrode. This is unlike the above noted patent application, U.S. patent application Ser. No. 13/644,485, incorporated herein by reference, where the diagnostic electrode(s) are immersed in electrolyte, structures which rely on diffusion in the liquid phase.

One solution to the need to confirm access of the ambient atmosphere, with the target gas and other components, to the target gas sensing electrode, is to use an auxiliary sensing electrode which is physically adjacent to the target gas sensing electrode. This auxiliary electrode can be used to detect a second gas, such as oxygen which is normally present as a background component. This structure could, for example, be implemented as in any of the designs of FIGS. 1 to 4B. In those figures, S-1 is the target gas sensing electrode, and D-1 is the second gas sensing diagnostic electrode. In all cases, the sensing electrode is of a relative size that causes the cell to operate in a diffusion limited mode based upon the use of the sensing electrode alone.

Such electrode structures could be screen printed or automatically puddled on a substrate, such as a flexible tape, T-1. The two electrodes could be the same material, for example, as in a CO sensor with an oxygen diagnostic electrode or two different materials.

Figure 3A:
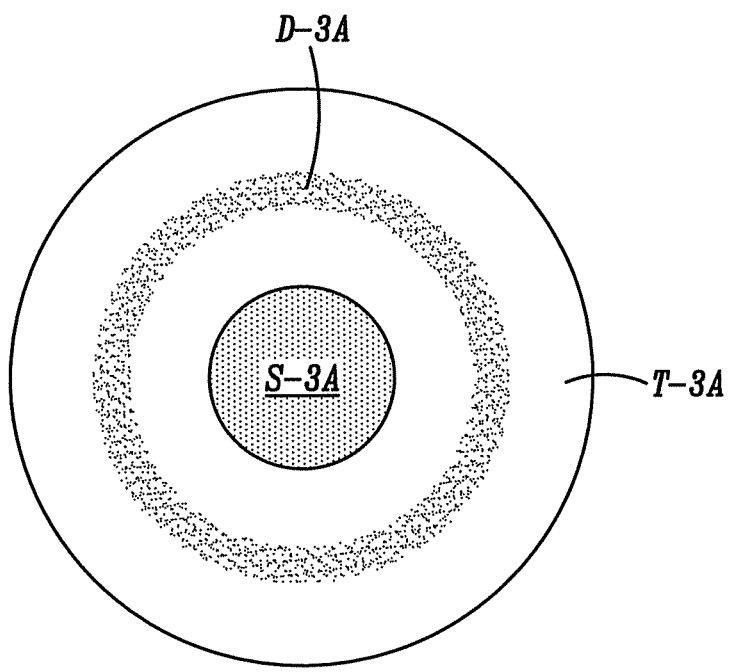
FIG. 3A illustrates a top planar view of yet another embodiment of sensing and diagnostic electrodes in accordance herewith.
Figure 3B:
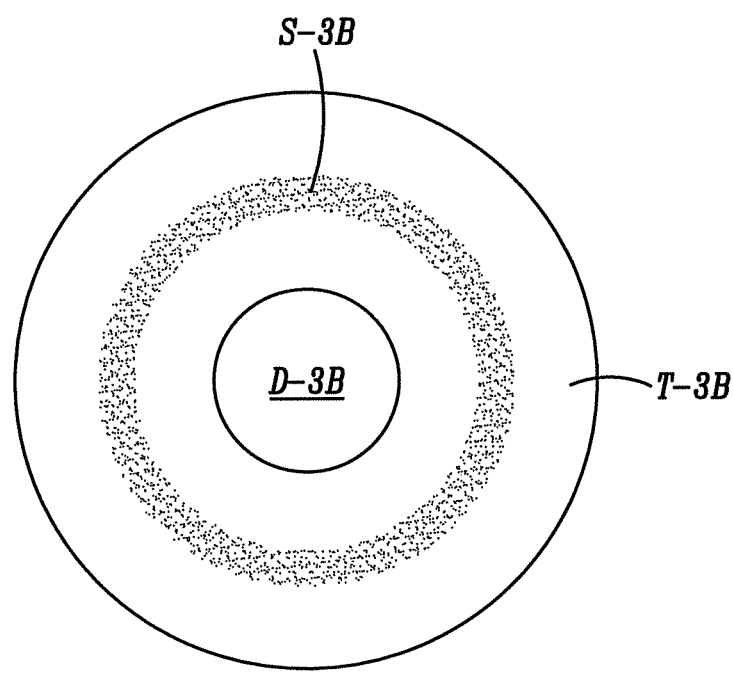
FIG. 3B illustrates a top planar view of a variation of the embodiment of FIG. 3A.
Figure 4A:
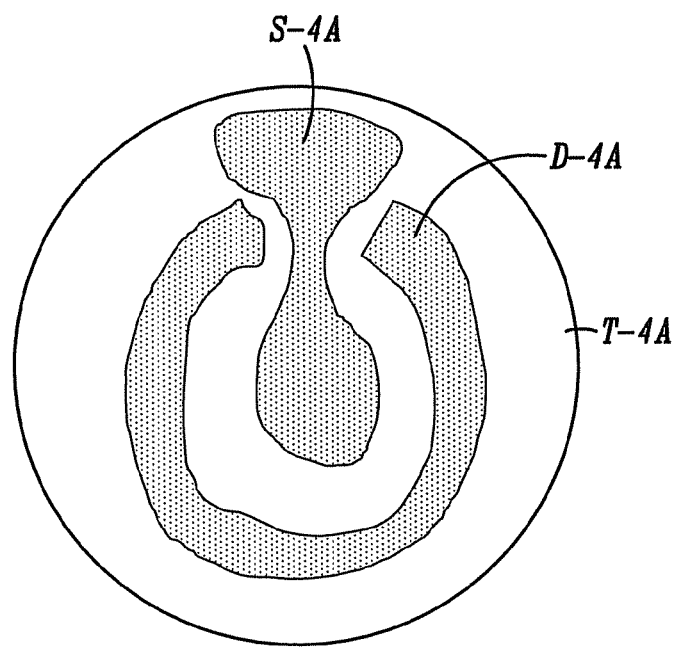
FIG. 4A illustrates a top planar view of yet another embodiment of sensing and diagnostic electrodes in accordance herewith.
Figure 4B:
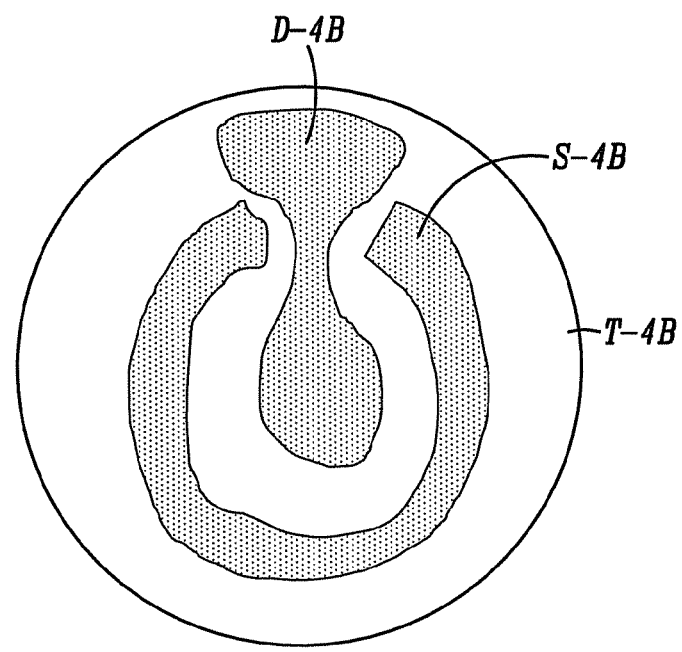
FIG. 4B illustrates a top planar view of a variation of the embodiment of FIG. 4A.
Figure 5:
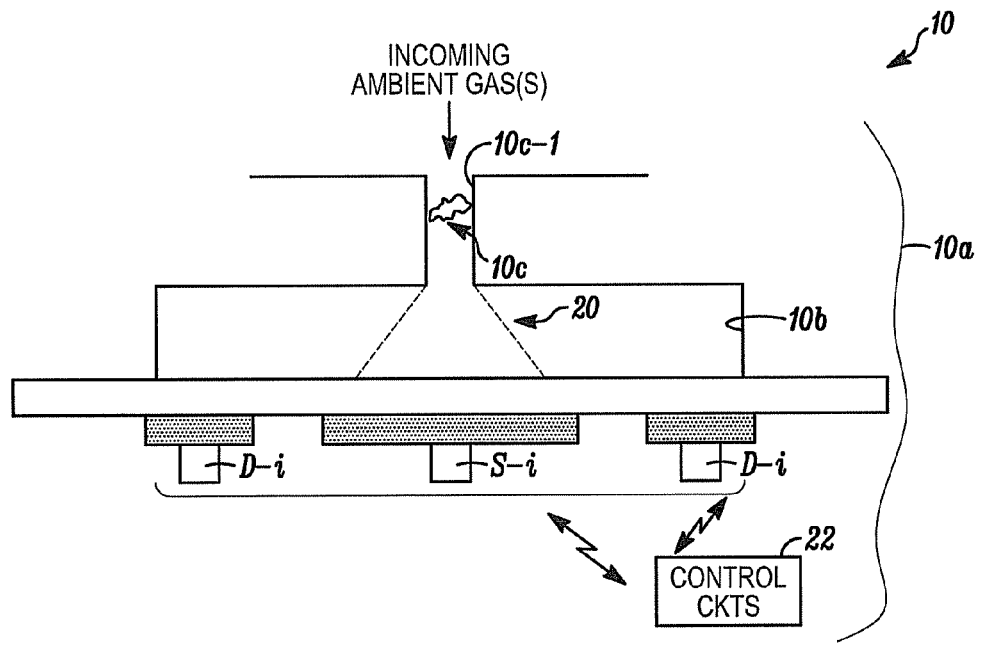
FIG. 5 illustrates a side sectional view of a portion of a gas sensor in accordance herewith.

A preferred implementation is shown in FIG. 5 whereby the electrodes are in the form of a disc and concentric ring (as in FIG. 3A,B or 4A,B). FIG. 5 illustrates a sensor 10 which has a housing 10a which defines a diffusion cavity 10b that has a diffusion barrier, such as a capillary, 10c positioned in ambient gas port 10c-1. Sensor 10 takes advantage of the fact that in current sensor designs the sensing electrode, such as Si, does not need to be the full diameter of the cavity 10b above it. Cavity 10b is, at least in part, located between the target gas diffusion barrier 10c and the target electrode S-i. It has been shown that the target gas, being consumed by the sensing electrode S-i, is almost entirely consumed by the central region of the sensing electrode, signified by the 'cone' 20, (as indicated by the dotted line) and that additional sensing electrode material outside this region is therefore unnecessary.

The diagnostic (or oxygen detecting) electrode, D-i, can then be concentric around the existing sensing electrode S-i. Note that the gas being detected as a diagnostic, for example oxygen, is not consumed by the sensing electrode S-i. Hence, it can be detected and consumed by the diagnostic electrode, D-i. The diagnostic electrode would not be operated continuously as the relatively large toxic sensor capillary would result in a very high oxygen signal. It would preferably be operated intermittently under the control of circuits 22 coupled thereto. Its steady state signal would give a direct measure of the capillary diffusion limitation (assuming oxygen concentration is known, measured or constant). It can also beneficially function in a transient mode as described in above noted published patent application US 2010/252455, previously incorporated by reference. There will be a background current present due to the presence of dissolved oxygen in the electrolyte but this will be small compared with the current due to oxygen entering through the capillary.

Figure 6:
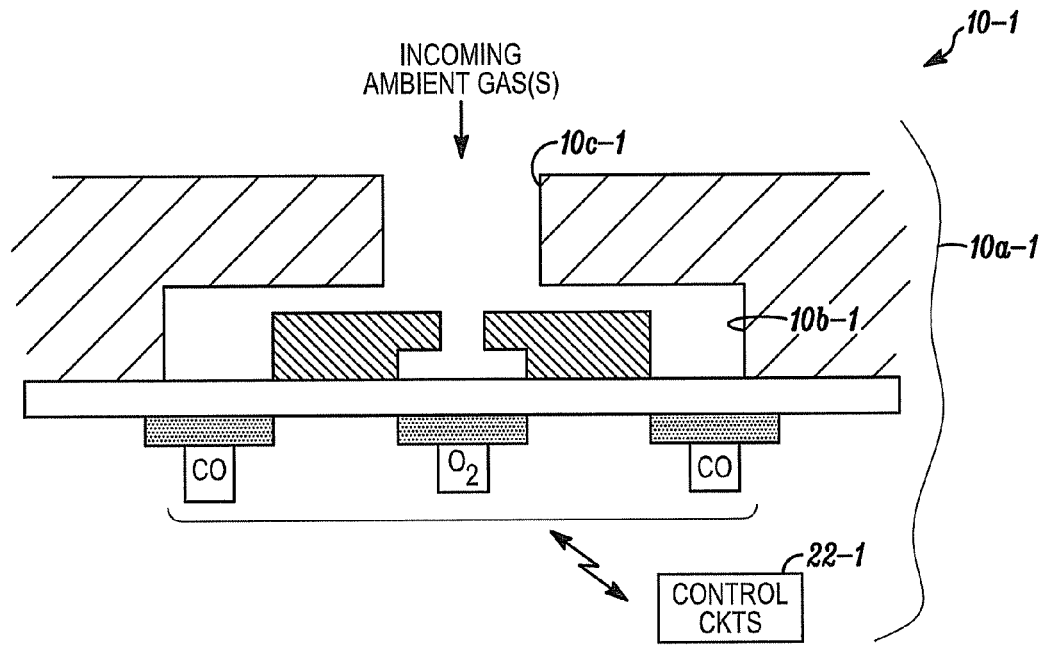
FIG. 6 illustrates a side sectional view of a portion of a different gas sensor in accordance herewith.
Figure 7:
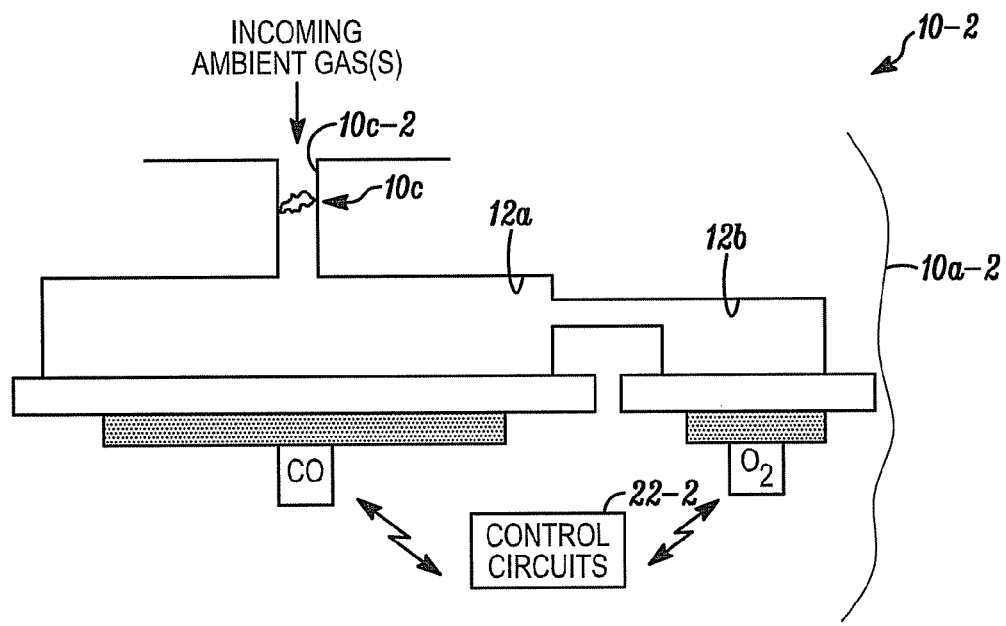
FIG. 7 illustrates a side sectional view of a portion of yet another gas sensor in accordance herewith.

FIGS. 6 and 7 show alternative approaches in sensors 10-1, 10-2. These configurations have the advantage of containing both an oxygen and a toxic, for example a CO, sensor whereby the oxygen sensor has its own diffusion limiter (capillary and/or membrane) but takes its gas sample from inside the cavity, such as 10b-1, or 12a of the toxic sensor. The disadvantage of this approach however is that the oxygen signal will not be very sensitive to restriction or blocking of the outer toxic sensor capillary unless the restriction or blocking is so severe that the diffusional restriction of the toxic sensor capillary becomes comparable to that of the oxygen sensor capillary.

Figure 8:
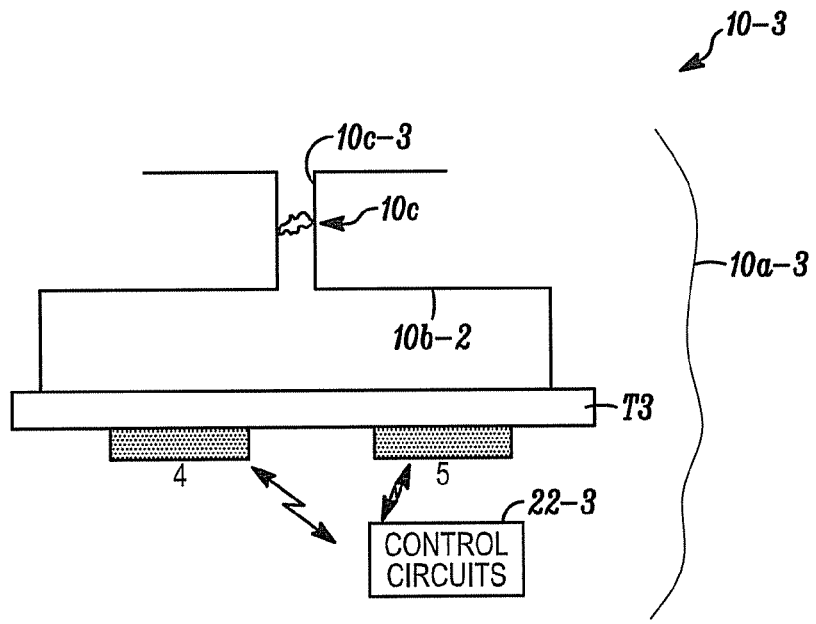
FIG. 8 illustrates a side sectional view of a portion of yet another gas sensor in accordance herewith.
Figure 9:
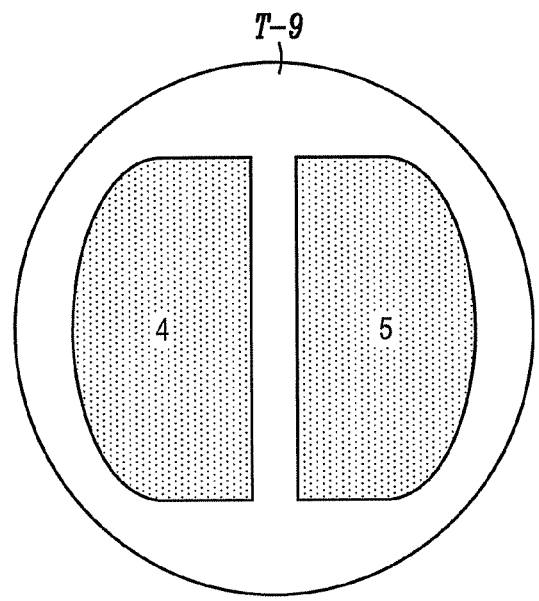
FIG. 9 illustrates a top planar view of sensing and diagnostic electrodes usable in the gas sensor of FIG. 8.
Figure 10:
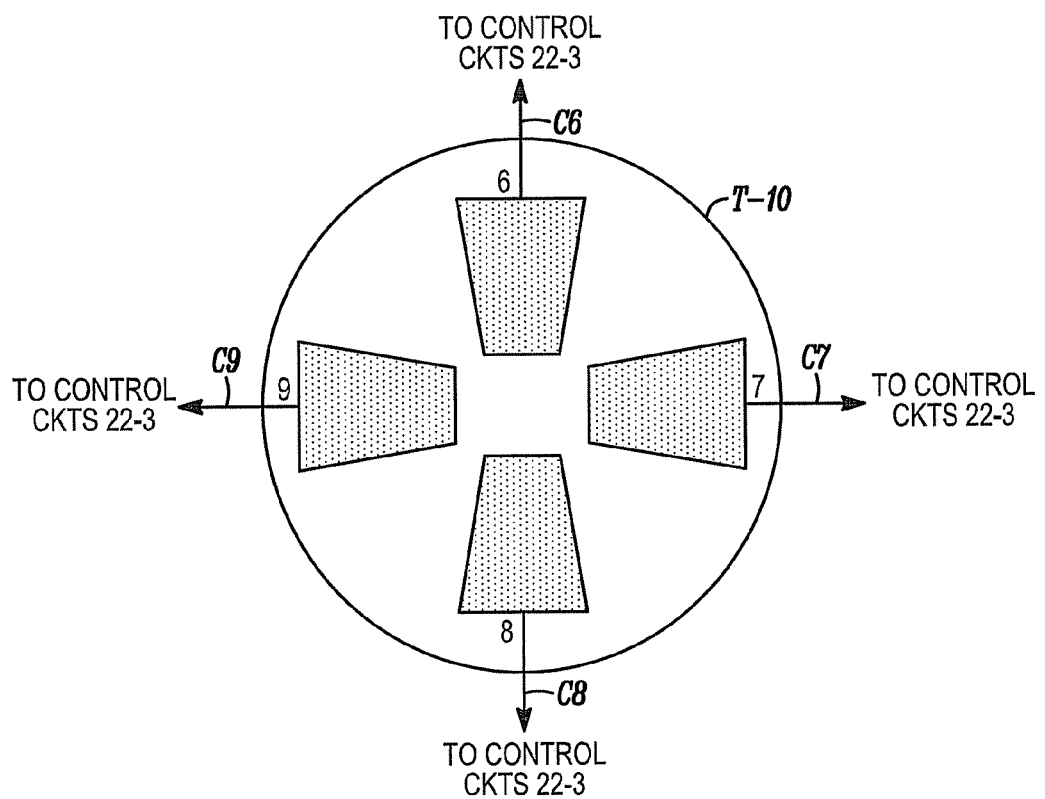
FIG. 10 illustrates a top planar view of alternate sensing and diagnostic electrodes usable in the gas sensor of FIG. 8.

We have further recognized that it is not necessary to have a sensing electrode that occupies the whole bottom face of the 'diffuser' cavity, 10b-2 in FIG. 8. Only small sensing electrodes, such as electrodes 4 or 5 in FIG. 8, are necessary to ensure a signal limited by capillary, 10c-3 and a target gas concentration near zero in cavity 10b-2. Therefore it is possible to have a multiplicity of electrodes, such as electrodes 4 and 5 which can be intermittently powered via control circuits 22-3. Any number of separate electrodes can potentially be incorporated, for example as in FIGS. 9 and 10, provided that the combination of electrodes operating at any given time has sufficient activity to maintain capillary diffusion limited behavior. In other words, such combinations of electrodes must be capable of fully consuming the capillary limited flux of the target gas reaching it.

With this type of structure, while one or more electrodes is operating, other electrode(s) may be performing different functions, including operating as diagnostic electrodes or being treated electrochemically for remediation purposes. Thus, control circuits 22-3 can switch, activate, or deactivate electrodes, both for sensing a target gas and the second, diagnostic gas to implement the various diagnostic methods discussed herein.

A similar concept can also be applied to any other electrodes within the sensor, for example multiple reference and or counter electrodes can be provided for similar reasons. A further benefit is that there is built in redundancy due to the use of multiple sensing electrodes. Since these can be operated alternately, any poisoning or degradation processes may occur differently on the different electrodes and hence drift in performance can be detected by comparison of the responses on the various electrodes.

Exemplary pluralities of electrodes, such as electrodes 4-9 in the FIGS. 8-10, are preferably deposited on a single support tape, such as tapes T1-T10, using selective deposition techniques such as direct puddling, screen printing, or puddling onto a temporary support followed by press transfer. Respective conductors, such as C6-C9 are used to electrically connect each of the electrodes 4-9 to the control circuits, such as 22-3.

From the foregoing, it will be observed that numerous variations and modifications may be effected without departing from the spirit and scope hereof. It is to be understood that no limitation with respect to the specific apparatus illustrated herein is intended or should be inferred. It is, of course, intended to cover by the appended claims all such modifications as fall within the scope of the claims. Further, logic flows depicted in the figures do not require the particular order shown, or sequential order, to achieve desirable results. Other steps may be provided, or steps may be eliminated, from the described flows, and other components may be added to, or removed from the described embodiments.

The invention claimed is:

1. A gas sensor comprising:
a housing defining an ambient gas port and a diffusion cavity, wherein the ambient gas port comprises a diffusion barrier;
a first sensing electrode configured to sense a target gas, wherein the target gas is not oxygen; and
a second sensing electrode configured to sense oxygen gas,
wherein the ambient gas port is the only entrance into the housing and the diffusion cavity,
wherein the diffusion cavity is located in a gaseous diffusion path between the ambient gas port and both the first sensing electrode and the second sensing electrode,
wherein the first sensing electrode and the second sensing electrode are in gaseous contact with the diffusion cavity,
wherein a flexible substrate carries the first sensing electrode and the second sensing electrode,
wherein the first sensing electrode and the second sensing electrode are co-planar,
wherein the first sensing electrode and the second sensing electrode are distributed symmetrically about an axis passing through the ambient gas port, and
wherein a plane of the first sensing electrode and the second sensing electrode is perpendicular to the axis passing through the ambient gas port.

2. The gas sensor as in claim 1, further comprising: control circuits electrically coupled to the first sensing electrode and the second sensing electrode.

3. The gas sensor as in claim 1, wherein the first sensing electrode and the second sensing electrode are each formed with one of a cylindrical shape, or an annular shape.

4. The gas sensor as in claim 1, wherein the first sensing electrode comprises a plurality of first electrodes or the second sensing electrode comprises a plurality of second electrodes.

5. The gas sensor as in claim 4, further comprising: control circuits coupled to the first sensing electrode and the second sensing electrode, wherein the control circuits are configured to cause the first sensing electrode to sense the target gas intermittently, and wherein the control circuits are further configured to cause the second sensing electrode to sense oxygen gas intermittently.

6. The gas sensor as in claim 5, wherein the control circuits are further configured to switch at least one of the first sensing electrode or the second sensing electrode from an active status to an inactive status.

7. The gas sensor as in claim 5, wherein the first sensing electrode and the second sensing electrode are formed with substantially the same shape.

8. The gas sensor as in claim 5, wherein the first sensing electrode and the second sensing electrode each have a surface area of a common size.

9. A gas sensor comprising:
a housing that defines an ambient gas port and an internal gas diffusion region for a target gas and oxygen gas;
a plurality of gas permeable sensing electrodes, carried by a flexible substrate, adjacent to the internal gas diffusion region, wherein the plurality of gas permeable sensing electrodes are in direct contact with the tar gas and the oxygen gas; and
control circuits electrically coupled to the plurality of gas permeable sensing electrodes,
wherein the ambient gas port is only the entrance to the internal gas diffusion region,
wherein the internal gas diffusion region is located between the ambient gas port and the plurality of gas permeable sensing electrodes, and
wherein the control circuits are configured to cause at least one electrode of the plurality of gas permeable sensing electrodes to intermittently sense the target gas and to cause at least one electrode of the plurality of gas permeable sensing electrodes to intermittently sense the oxygen gas.

10. The gas sensor as in claim 9, wherein each of the plurality of gas diffusion sensing electrodes has a same shape.

11. The gas sensor as in claim 10, wherein each of the plurality of gas diffusion sensing electrodes surround a common line, wherein the common line extends perpendicular to a plane of the flexible substrate and asses through the ambient gas port.

12. The gas sensor as in claim 11, wherein the control circuits are configured to select at least one electrode to sense the target gas for a first time interval and at least a second electrode to sense the target gas for a second time interval, and wherein the control circuits are further configured to select a third electrode to sense the oxygen gas for a first diagnostic time interval and a fourth electrode to sense the oxygen gas for a second diagnostic time interval.

13. The gas sensor as in claim 9, wherein the control circuits are configured to use a selected electrode for sensing the target gas during one time interval and for sensing the oxygen gas during another time interval.

14. A gas sensor comprising:
a housing defining an ambient gas port and a diffusion cavity;
a diffusion barrier disposed between the gas port and the diffusion cavity;
a first sensing electrode configured to sense a target gas, wherein the target gas is not oxygen;
a second sensing electrode configured to sense oxygen; and
a counter electrode separated from the first sensing electrode and the second sensing electrode by a separator,
wherein the first sensing electrode and the second sensing electrode are in gaseous contact with the diffusion cavity,
wherein the first sensing electrode and the second sensing electrode are co-planar, and
wherein the first sensing electrode and the second sensing electrode are distributed symmetrically about an axis passing through the ambient gas port.

15. The gas sensor of claim 14, wherein the ambient gas port is the only entrance into the housing and the diffusion cavity.

16. The gas sensor of claim 15, wherein the diffusion cavity is located in a gaseous diffusion path between the ambient gas port and both the first electrode and the second electrode.

17. The gas sensor of claim 14, wherein a plane of the first electrode and the second electrode is perpendicular to the axis passing through the ambient gas port.

18. The gas sensor of claim 14, wherein the first sensing electrode and the second sensing electrode comprise gas diffusion electrodes.

* * * * *